(12) United States Patent
Klemann et al.

(10) Patent No.: US 8,911,813 B2
(45) Date of Patent: *Dec. 16, 2014

(54) STRUCTURED LIPID COMPOSITIONS

(71) Applicant: Intercontinental Great Brands LLC, East Hanover, NJ (US)

(72) Inventors: Lawrence Paul Klemann, Annandale, NJ (US); Robert C. Dinwoodie, Glenview, IL (US)

(73) Assignee: Intercontinental Great Brands LLC, East Hanover, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/913,825

(22) Filed: Jun. 10, 2013

(65) Prior Publication Data
US 2013/0280408 A1 Oct. 24, 2013

Related U.S. Application Data

(63) Continuation of application No. 11/937,080, filed on Nov. 8, 2007, now Pat. No. 8,486,478.

(51) Int. Cl.
| | | |
|---|---|---|
| *A23D 9/00* | (2006.01) | |
| *A23D 9/007* | (2006.01) | |
| *C11C 3/10* | (2006.01) | |
| *A23D 9/02* | (2006.01) | |
| *C11C 3/02* | (2006.01) | |
| *A23L 1/30* | (2006.01) | |

(52) U.S. Cl.
CPC ............ *A23D 9/00* (2013.01); *C12Y 301/01003* (2013.01); *C11C 3/10* (2013.01); *A23D 9/02* (2013.01); *C11C 3/02* (2013.01); *A23L 1/3006* (2013.01)
USPC ............................ 426/606; 426/607; 426/611

(58) Field of Classification Search
USPC .................... 426/601, 606, 607, 611
See application file for complete search history.

(56) References Cited

U.S. PATENT DOCUMENTS

| | | |
|---|---|---|
| 2,614,937 A | 10/1952 | Baur |
| 2,615,159 A | 10/1952 | Jackson |
| 2,615,160 A | 10/1952 | Baur |
| 3,192,057 A | 6/1965 | Russell |
| 3,388,085 A | 6/1968 | Henry |
| 3,808,245 A | 4/1974 | OConner |
| 4,272,548 A | 6/1981 | Gatzen |
| 4,341,813 A | 7/1982 | Ward |
| 4,364,868 A | 12/1982 | Hargreaves |
| 4,390,561 A | 6/1983 | Blair |
| 4,436,760 A | 3/1984 | Verhagen |
| 4,447,462 A | 5/1984 | Tafuri |
| 4,479,976 A | 10/1984 | Lansbergen |
| 4,486,457 A | 12/1984 | Schijf |
| 4,504,503 A | 3/1985 | Biernoth |
| 4,567,056 A | 1/1986 | Schmidt |
| 4,671,963 A | 6/1987 | Germino |
| 4,832,975 A | 5/1989 | Yang |
| 4,839,190 A | 6/1989 | Bumbalough |
| 4,839,192 A | 6/1989 | Sagi |
| 4,865,866 A | 9/1989 | Moore |
| 4,873,109 A | 10/1989 | Tanaka |
| 4,880,646 A | 11/1989 | Lew |
| 4,883,684 A | 11/1989 | Yang |
| 4,915,971 A | 4/1990 | Fennema |
| 5,064,670 A | 11/1991 | Hirshorn |
| 5,066,510 A | 11/1991 | Ehrman |
| 5,071,669 A | 12/1991 | Seiden |
| 5,130,151 A | 7/1992 | Averbach |
| 5,142,071 A | 8/1992 | Kluesener |
| 5,142,072 A | 8/1992 | Stipp |
| 5,240,726 A | 8/1993 | Zook |
| 5,258,197 A | 11/1993 | Wheeler |
| 5,268,198 A | 12/1993 | Yamasaki |
| 5,288,512 A | 2/1994 | Seiden |
| 5,288,619 A | 2/1994 | Brown |
| 5,312,836 A | 5/1994 | Bistrian |
| 5,362,508 A | 11/1994 | Wheeler |
| 5,374,438 A | 12/1994 | Yost |
| 5,378,490 A | 1/1995 | Wheeler |
| 5,380,544 A | 1/1995 | Klemann |
| 5,382,440 A | 1/1995 | Sullivan |

(Continued)

FOREIGN PATENT DOCUMENTS

| | | |
|---|---|---|
| CA | 2212467 C | 2/1998 |
| EP | 0322027 A2 | 6/1989 |

(Continued)

OTHER PUBLICATIONS

'MultOil: A Multi-functional oil for the food industry.' Enzymotec Ltd, Migdal HaEmeq, Israel, believed to be published at least by about 2003, 4 pages.
'Solid Fat Content (SFC) by Low Resolution Nuclear Magnetic Resonance—The Direct Method,' Sampling and Analysis of Commercial Fats and Oils, AOCS Official Method Cd 16b-93, Revised 1999, pp. 1-10.
Anthony M. Ambrose and Dorothy J. Robbins, 'Studies on Comparative Absorption and Digestibility of Acetoglycerides,' Journal of Nutrition, vol. 58, 1956, pp. 113-124.

(Continued)

*Primary Examiner* — Carolyn Paden
(74) *Attorney, Agent, or Firm* — Fitch, Even, Tabin & Flannery LLP

(57) ABSTRACT

Lipid compositions are provided exhibiting the functionality of a typical shortening or filler fat, but are achieved with reduced and essentially zero trans-unsaturated fatty acids and that deliver reduced caloric content. By one approach, the functional lipid compositions include a blend of a matrix building ingredient, which is preferably a structured glycerol ester, and an edible liquid oil diluent in ratios such that the lipid composition exhibits the functionality of the traditional shortening or filler fat.

19 Claims, No Drawings

(56) References Cited

U.S. PATENT DOCUMENTS

| | | | |
|---|---|---|---|
| 5,391,383 A | 2/1995 | Sullivan |
| 5,407,695 A | 4/1995 | Wheeler |
| 5,411,756 A | 5/1995 | Wheeler |
| 5,419,925 A | 5/1995 | Seiden |
| 5,422,131 A | 6/1995 | Elsen |
| 5,434,278 A | 7/1995 | Pelloso |
| 5,456,939 A | 10/1995 | Wheeler |
| 5,458,910 A | 10/1995 | Gruetzmacher |
| 5,470,598 A | 11/1995 | Scavone |
| 5,490,995 A | 2/1996 | Corrigan |
| 5,492,714 A | 2/1996 | Guskey |
| 5,504,231 A | 4/1996 | Guskey |
| 5,552,174 A | 9/1996 | Wheeler |
| 5,565,232 A | 10/1996 | Wheeler |
| 5,589,216 A | 12/1996 | Guskey |
| 5,589,217 A | 12/1996 | Mazurek |
| 5,612,080 A | 3/1997 | Gruetzmacher |
| 5,624,703 A | 4/1997 | Perlman |
| 5,662,953 A | 9/1997 | Wheeler |
| 5,683,738 A | 11/1997 | Gruetzmacher |
| 5,843,497 A | 12/1998 | Sundram |
| 5,863,589 A | 1/1999 | Covington |
| 5,879,735 A | 3/1999 | Cain |
| 5,912,042 A | 6/1999 | Cain |
| 5,962,062 A | 10/1999 | Carrie |
| 6,022,577 A | 2/2000 | Chrysam |
| 6,033,703 A | 3/2000 | Roberts |
| 6,106,879 A | 8/2000 | Mori |
| 6,106,885 A | 8/2000 | Huizinga |
| 6,140,520 A | 10/2000 | Hartel |
| 6,238,723 B1 | 5/2001 | Sassen |
| 6,238,926 B1 | 5/2001 | Liu |
| 6,277,432 B1 | 8/2001 | Chang |
| 6,369,252 B1 | 4/2002 | Akoh |
| 6,827,963 B2 | 12/2004 | Aoyama |
| 7,229,653 B2 | 6/2007 | Sundram |
| 7,241,468 B2 | 7/2007 | Naber |
| 7,517,545 B2 | 4/2009 | Kaimal |
| 8,206,772 B2 * | 6/2012 | Klemann et al. ............ 426/606 |
| 8,486,478 B2 * | 7/2013 | Klemann et al. ............ 426/606 |
| 2002/0192318 A1 | 12/2002 | Berry |
| 2003/0143312 A1 | 7/2003 | Tamarkin |
| 2003/0215556 A1 | 11/2003 | Naber |
| 2004/0043125 A1 | 3/2004 | Kaimal |
| 2004/0049813 A1 | 3/2004 | Russell |
| 2004/0052898 A1 | 3/2004 | Yatka |
| 2004/0101601 A1 | 5/2004 | Loh |
| 2004/0122246 A1 | 6/2004 | Sparso |
| 2004/0166204 A1 | 8/2004 | Smith |
| 2004/0170720 A1 | 9/2004 | Yatka |
| 2005/0163909 A1 | 7/2005 | Cleenewerck |
| 2006/0154986 A1 | 7/2006 | Finley |
| 2007/0082112 A1 | 4/2007 | Kincs |
| 2007/0172573 A1 | 7/2007 | Higgins |
| 2007/0178218 A1 | 8/2007 | Yager |
| 2007/0185340 A1 | 8/2007 | Van Toor et al. |
| 2007/0231446 A1 | 10/2007 | Nagasawa |
| 2007/0243308 A1 | 10/2007 | Yu |
| 2007/0269468 A1 | 11/2007 | Bach |
| 2009/0123632 A1 | 5/2009 | Klemann |
| 2009/0123634 A1 | 5/2009 | Klemann |

FOREIGN PATENT DOCUMENTS

| | | |
|---|---|---|
| EP | 0390410 A2 | 10/1990 |
| EP | 0505408 B1 | 9/1992 |
| EP | 0506739 B1 | 10/1992 |
| EP | 0666839 | 8/1995 |
| EP | 0793421 | 9/1997 |
| EP | 1051903 | 11/2000 |
| EP | 1586242 | 10/2005 |
| EP | 1676484 | 7/2006 |
| EP | 1759589 | 3/2007 |
| EP | 1783200 | 9/2007 |
| EP | 2057902 | 5/2009 |
| GB | 816343 | 7/1959 |
| GB | 822730 | 10/1959 |
| GB | 2239256 | 6/1991 |
| JP | 64019042 | 1/1989 |
| JP | 02158695 | 6/1990 |
| JP | 2001139983 | 5/2001 |
| JP | 2002095426 | 4/2002 |
| JP | 2005237319 | 9/2005 |
| JP | 2006288233 | 10/2006 |
| JP | 2007215521 | 8/2007 |
| WO | 9103944 | 4/1991 |
| WO | 9109098 | 6/1991 |
| WO | 9109099 | 6/1991 |
| WO | 9110368 | 7/1991 |
| WO | 9115126 | 10/1991 |
| WO | 9201394 | 2/1992 |
| WO | 9210105 | 6/1992 |
| WO | 9215200 | 9/1992 |
| WO | 9300016 | 1/1993 |
| WO | 9410126 | 5/1994 |
| WO | 9412051 | 6/1994 |
| WO | 9416573 | 8/1994 |
| WO | 9419961 | 9/1994 |
| WO | 9632022 | 10/1996 |
| WO | 9723538 | 7/1997 |
| WO | 9819554 | 5/1998 |
| WO | 0015043 | 3/2000 |
| WO | 0143558 | 6/2001 |
| WO | 02102169 A2 | 12/2002 |
| WO | 2004039929 | 5/2004 |
| WO | 2005011391 | 2/2005 |
| WO | 2005053767 | 6/2005 |
| WO | 2005122777 | 12/2005 |
| WO | 2006002273 | 1/2006 |
| WO | 2006005141 | 1/2006 |
| WO | 2006029139 | 3/2006 |
| WO | 2006052870 | 5/2006 |
| WO | 2006053097 | 5/2006 |
| WO | 2006059592 | 6/2006 |
| WO | 2006076433 | 7/2006 |
| WO | 2007015519 | 2/2007 |
| WO | 2007037370 | 4/2007 |
| WO | 2007141222 | 12/2007 |

OTHER PUBLICATIONS

Arunabh Bhattacharya et al., 'The Combination of Dietary Conjugated Linoleic Acid and Treadmill Exercise Lowers Gain in Body Fat Mass and Enhances Lean Body Mass in High Fat Fed Male Balb/C Mice,' Journal of Nutrition, vol. 135, 2005, pp. 1124-1130.

Casimir C. Akoh and Barry G. Swanson, 'Preparation of Trehalose and Sorbitol Fatty Acid Polyesters by Interesterification,' Journal of the American Oil Chemists' Society, vol. 66, No. 11, Nov. 1989, pp. 1581-1587.

Casimir C. Akoh and Kuan-Hsiang Huang, 'Enzymatic Synthesis of Structured Lipids: Tranesterification of Triolein and Caprylic Acid,' Journal of Food Lipids, vol. 2, Issue 4, Dec. 1995, pp. 219-230.

Chi-Sun Wang et al., 'Studies on the Substrate Specificity of Purifed Human Milk Bile Salt-activated Lipase,' Journal of Biological Chemistry, vol. 258, No. 15, Aug. 10, 1983, pp. 9197-9202.

David Jago, 'Health Begets Wealth,' Prepared Foods, Apr. 2001, pp. 21-22.

E. D. Wills, 'Studies on the Purification and Specificity of Pancreatic Lipase,' The Enzymes of Lipid Metabolism, Pergamon Press, New York, 1961, pp. 13-19.

Emile A. M. de Deckere et al., 'Effects of conjugated linoleic acid (CLA) isomers on lipid levels and peroxisome proliferation in the hamster,' British Journal of Nutrition, vol. 82, No. 4, 1999, pp. 309-317.

European Examination Report, European Patent Application No. 08 168 426.8, dated May 2, 2011, 4 pages.

European Patent No. EP2057904, Notice of Opposition by Nestec SA, 19 pages.

European Patent Office Extended European Search Report for European Application No. 08168426.8 dated Feb. 6, 2009 (10 pages).

European Patent Office Extended Search Report for European Application No. 08167992.0 dated Feb. 25, 2009 (12 pages).

(56) References Cited

OTHER PUBLICATIONS

European Search Report for EP Application No. 08168422, dated Mar. 27, 2009.
Extended European Search Report, European Patent Application No. 11191819.9, date of completion of the search May 2, 2012, 7 pages.
F. H. Mattson, 'The Absorbability of Stearic Acid When Fed as a Simple or Mixed Triglyceride,' Journal of Nutrition, vol. 69, 1959, pp. 338-342.
F. H. Mattson et al., 'Short-Term Feeding Studies on Acetin Fats,' Journal of Nutrition, vol. 59, No. 2, Jun. 1956, pp. 277-285.
F. L. Jackson, R. L. Wille, and E. S. Lutton, 'The Polymorphism of 2-Acetyl-, 2-Butyryl- and 2-Caproyldistearin and -dipalmitin,' Journal of the American Chemical Society, vol. 73, 1951, pp. 4280-4284.
F. L. Jackson and E. S. Lutton, 'The Polymorphism of 1-Stearyl- and 1-Palmityldiacetin, -dibutyrin, -dicaproin and 1-Stearyldipropionin,' Journal of the American Chemical Society, vol. 74, Oct. 5, 1952, pp. 4827-4829.
Fred H. Mattson, Granville A. Nolen, and Marjorie R. Webb, 'The Absorbability by Rats of Various Triglycerides of Stearic and Oleic Acid and the Effect of Dietary Calcium and Magnesium,' Journal of Nutrition, vol. 109, 1979, pp. 1682-1687.
Fred J. Baur, 'Acetin Fats. I. Products Made from Mixed Acetin Fats,' Journal of the American Oil Chemists' Society, vol. 31, Apr. 1954, pp. 147-151.
Freeman, C. 1965. Journal of Dairy Science 48(7)853-858.
Fritz Schnheyder and Kirsten Volqvartz, 'On the Activity of Lipases Toward Triglycerides,' Enzymologia Acta Biocatalytica, Elsevier Publishing Company Inc., New York, vol. XI, 1943, pp. 178-185.
G. Clement, J. Clement, and J. Bezard, 'Action of Human Pancreatic Lipase on Synthetic Mixed Symmetrical Triglycerides of Long-Chain Acids and Butyric Acid,' Biochemical and Biophysical Research Communications, vol. 8, No. 3, 1962, pp. 238-242.
G.R. List et al., 'Margarine and Shortening Oils by Interesterification of Liquid and Trisaturated Triglycerides.' Journal of the American Oil Chemists' Society, vol. 72, No. 3, 1995, pp. 379-382.
G.R. List et al., 'Preparation and Properties of Zero Trans Soybean Oil Margarines.' Journal of the American Oil Chemists' Society, vol. 72, No. 3, 1995, pp. 983-984.
Ghosh et al., Moisture Migration Through Chocolate-Flavored Confectionery Coatings, 66 Journal of Food Engineering, 177-186 (2005).
Gresti, J. et al. 1993. Journal of Dairy Science 76:1850.
H. C. Eckstein, 'The Influence of Diet on the Body Fat of the White Rat,' Journal of Biological Chemistry, vol. 81, 1929, pp. 613-628.
H. J. Deuel, Jr., 'III. Digestibility of Fats,' The Lipids: Their Chemistry and Biochemistry, vol. II, Interscience Publishers, 1955, pp. 218-227.
H. T. Osborn and C. C. Akoh, 'Structured Lipids-Novel Fats with Medical, Nutraceutical, and Food Applications,' Comprehensive Reviews in Food Science and Food Safety, vol. 3, Jan. 2002, pp. 93-103.
H.M.D. Noor Lida et al., 'TAG Composition and Solid Fat Content of Palm Oil, Sunflower Oil, and Palm Kernel Olein Blends Before and After Chemical Interesterification.' Journal of the American Oil Chemists' Society, Nov. 2002, vol. 79, No. 11, pp. 1137-1144.
Hans Kaunitz et al., 'Nutritional Properties of the Triglycerides of Saturated Fatty Acids of Medium Chain-Length,' Journal of the American Oil Chemists' Society, vol. 35, Jan. 1958, pp. 10-13.
Harry Sobotka and David Glick, 'Lipolytic Enzymes: 1. Studies on the Mechanism of Lipolytic Enzyme Actions,' Journal of Biological Chemistry, vol. 105, 1934, pp. 199-219.
Herbert A. Ravin and Arnold M. Seligman, 'Determinants for the Specificity of Action of Pancreatic Lipase,' Archives of Biochemistry and Biophysics, Academic Press, Inc., vol. 42, No. 2, Feb. 1953, pp. 337-354.
I. Greener Donhowe et al., 'The Effect of Relative Humidity Gradient on Water Vapor Permeance of Lipid and Lipid-Hydrocolloid Bilayer Films,' Journal of the American Oil Chemists' Society, 1992, vol. 69, No. 11, pp. 1081-1087.

Ikuo Ikeda, 'Digestion and Absorption of Structured Lipids,' Fat Digestion and Absorption, American Oil Chemists' Society, Illinois, 2000, Chapter 11, pp. 235-243.
Iwona Rudkowska et al., 'Phytosterols mixed with medium-chain triglycerides and high-oleic canola oil decrease plasma lipids in overweight men,' Metabolism Clinical and Experimental, vol. 55, 2006, pp. 391-395.
J. H. Cummings, 'Short chain fatty acids in the human colon,' Gut, vol. 22, 1981, pp. 763-779.
J.W. McAtee, C. O. Little, and G. E. Mitchell, Jr., 'Utilization of Rumen Metabolites as Energy Sources in Rats.' Life Sciences, vol. 7, No. 14, 1968, pp. 769-775.
James F. Mead et al., 'Nutritional Value of Lipids,' Lipids Chemistry, Biochemistry, and Nutrition, Plenum Press, New York, 1986, Chapter 19, pp. 459-473.
James P. Miller, 'ADM to enter joint venture for cooking oil,' Chicago Tribune, Jun. 13, 2001, 2 pages.
Joanne P. Kennedy, 'Structured Lipids: Fats of the Future,' Food Technology, Nov. 1991, pp. 76-83.
John M. Deman, 'Relationship Among Chemical, Physical and Textural Properties of Fats.' Chapter 5, pp. 79-95, Physical Properties of Fats, Oils and Emulsifiers, Ed. Neil Widlak (1999).
John W. Finley et al., 'Growth Method for Estimating the Caloric Availability of Fats and Oils,' Journals of Agricultural and Food Chemistry, vol. 42, No. 2, 1994, pp. 489-494.
Johnnie R. Hayes et al., 'In Vivo Metabolism of Salatrim Fats in the Rat,' Journal of Agricultural and Food Chemistry, vol. 42, No. 2, 1994, pp. 500-514.
Journal of Agricultural and Food Chemistry, American Chemical Society, vol. 42, No. 2, Feb. 1994, pp. 432-604.
Junichi Ozaki, 'Uber den relativen Nhrwert der synthetischen Fette,' Biochemische Zeitschrift, 177, Berlin, 1926, pp. 156-167.
K. K. Carroll, 'Digestibility of Individual Fatty Acids in the Rat,' Journal of Nutrition, vol. 64, 1958, pp. 399-410.
Kartha, A. 1968, JAOCS 45:101.
Kevin C. Maki et al., 'Consumption of diacylglycerol oil as part of a reduced-energy diet enhances loss of body weight and fat in comparison with consumption of a tricylglycerol control oil,' American Journal of Clinical Nutrition, vol. 76, 2002, pp. 1230-1236.
Ki-Teak Lee and Casimir C. Akoh, 'Characterization of Enzymatically Synthesized Structured Lipids Containing Eicosapentaenoic, Docosahexaenoic, and Caprylic Acids,' Journal of the American Oil Chemists' Society, vol. 75, No. 4, Apr. 1998, pp. 495-499.
Kuan-Hsiang Huang et al., 'Enzymatic Synthesis of Structured Lipids: Transesterification of Triolein and Caprylic Acid Ethyl Ester.' Journal of the American Oil Chemists' Society, vol. 73, No. 2, 1996, pp. 245-250.
L. Emmett Holt, Jr. et al., 'Studies in Fat Metabolism,' Journal of Pediatrics, vol. 6, No. 4, Apr. 1935, pp. 427-480.
L. P. Klemann et al., 'Estimation of the Absorption Coefficient of Stearic Acid in Salatrim Fats,' Journal of Agricultural and Food Chemistry, vol. 42, No. 2, 1994, pp. 484-488.
Lawrence P. Klemann, 'Effects of Interesterification on the Physical Properties of Fats,' Abstract of presentation at the AOCS International Conference on the Physical Properties of Fats, Oils and Emulsifiers, Chicago, Illinois, Sep. 1997, one page.
Lawrence P. Klemann et al., 'Random Nature of Triacylglycerols Produced by the Catalyzed Interesterification of Short- and Long-Chain Fatty Acid Triglycerides,' Journal of Agricultural and Food Chemistry, vol. 42, No. 2, 1994, pp. 442-446.
Life Sciences Research Office, 'The Evaluation of the Health Aspects of Using Certain Triacylglycerols as Food Ingredients,' Federation of American Societies for Experimental Biology, Maryland, Aug. 1993, 73 pages.
Lydia B. Fomuso et al., 'Enzymatic Modification of Triolein: Incorporation of Caproic and Butyric Acids to Produce Reduced-Calorie Structured Lipids.' Journal of the American Oil Chemists' Soceity, vol. 74, No. 3, 1997, pp. 269-272.
M.N. Auerbach et al., 'Salatrim: A Family of Reduced-Calorie Structured Lipids,' Chapter 5, pp. Structural Modified Fats: Synthesis, Biochemistry and Use; Ed. Armand Christophe, American Oil Chemists' Society, Publishing, 1998, pp. 89-116.

(56) References Cited

OTHER PUBLICATIONS

Mark Dreher et al., 'Salatrim: A Triglyceride-Based Fat Replacer,' Nutrition Today, vol. 33, No. 4, Jul./Aug. 1998, pp. 164-170.
Martin Anker et al., 'Improved Water Vapor Barrier of Whey Protein Films by Addition of an Acetylated Monoglyceride.' Innovative Food Science & Emerging Technologies, vol. 3, 2002, pp. 81-92.
Marvin W. Formo et al., 'Fatty Acids,' Bailey's Industrial Oil and Fat Products, vol. 1, Fourth Edition, John Wiley & Sons, New York, 1979, pp. 16-17.
Meyer, L. H. 1960. Food Chemistry. Reinhold Publishing Corporation, New York. p. 33.
Michael H. Auerbach, Lawrence P. Klemann, and Jenifer a. Heydinger, 'Reduced-Energy Lipids,' Structured and Modified Lipids, CRC Press, New York, 2001, Chapter 18, pp. 485-510.
Mimma Pernetti et al., 'Structuring of Edible Oils by Alternatives to Crystalline Fat.' Current Opinion in Colloid & Interface Science, vol. 12, 2007, pp. 221-231.
N. V. Lovegren and M. S. Gray, 'Polymorphism of Saturated Triglycerides: I. 1,3-Distearo Triglycerides,' Journal of the American Oil Chemists' Society, vol. 55, Mar. 1978, pp. 310-316.
P. Desnuelle and P. Savary, 'Specificities of Lipases,' Journal of Lipid Research, vol. 4, No. 4, Oct. 1963, pp. 369-384.
P. S. MacLean et al., 'Caloric Availability of Fats,' Center for Human Nutrition, Univeristy of Colorado HSC, Kraft Foods Sponsored Research, Jan. 4, 2004, 13 pages.
Paul S. MaClean et al., 'Metobolic adjustment with the development, treatment, and recurrence of obesity in obesity-prone rats,' American Journal of Physiology—Regulatory, Integrative and Comparative Physiology, vol. 287, Aug. 2004, pp. R288-R297.
R. D. Coleman, L. A. Gayle, and Roslyn B. Alfin-Slater, 'A Nutritional Evaluation of Acetostearins in Rats,' Journal of the American Oil Chemists' Society, vol. 40, Dec. 1963, pp. 737-742.
R. M. Tomarelli et al., 'Effect of Positional Distribution on the Absorption of the Fatty Acids of Human Milk and Infant Formulas,' Journal of Nutrition, vol. 95, 1968, pp. 583-590.
R. O. Feuge, 'Acetoglycerides—New Fat Products of Potential Value to the Food Industry,' Food Technology, vol. 9, 1955, pp. 314-318.
Robyn M. Treadwell et al., 'Glyceride Stearic Acid Content and Structure Affect the Energy Available to Growing Rats,' Journal of Nutrition, vol. 132, 2002, pp. 3356-3362.
Ronald P. Mensink and Martijn B. Katan, 'Effect of Dietary Trans Fatty Acids on High-Density and Low-Density Lipoprotein Cholesterol Levels in Healthy Subjects,' New England Journal of Medicine, vol. 323, No. 7, Aug. 16, 1990, pp. 439-445.
S. S. Weinstein and A. M. Wynne, 'Studies on Pancreatic Lipase II. Influence of Various Components on the Hydrolytic Activity,' Journal of Biological Chemistry, vol. 112, 1936, pp. 649-660.
Salatrim Data Sheet, 2002, prepared at the 59th JECFA (2002) and published in FNP 52 Add 10, (12 pages).
Sami A. Hashim and Vigen K. Babayan, 'Studies in man of partially absorbed dietary fats,' American Journal of Clinical Nutrition, vol. 31, Oct. 1978, pp. S273-S276.
Selma E. Snyderman, Soledad Morales, and L. Emmett Holt, Jr., 'Premature Infants,' Archives of Disease in Childhood, British Medical Association, London, vol. XXX, 1955, pp. 83-84
Swern, D. 1979. Baileys Industrial Oil and Fat Products, vol. 1, 4th edition. p. 348-349.
Swern, D. editor. 'Bailey's Industrial Oil and Fat Products.' vol. 1, 4th edition, John Wiley & Sons, New York, 1979, pp. 378-379.
V. K. Babayan, 'Medium Chain Triglycerides,' Dietary Fat Requirements in Healt and Development, American Oil Chemists' Society, Illinois, 1988, Chapter 5, pp. 73-86.
V. Petrauskaite et al., 'Physical and Chemical Properties of trans-Free Fats Produced by Chemical Interesterification of Vegetable Oil Blends.' Journal of the American Oil Chemists' Society, vol. 75, No. 4, 1998, pp. 489-493.
Valerie Morillion et al., 'Factors Affecting the Moisture Permeability of Lipid-Based Edible Films: A Review,' Critical Reviews in Food Science and Nutrition, vol. 42, No. 1, 2002, pp. 67-89.
Wai-Lin Stew et al., 'Effect of Diglycerides on the Crystallisation of Palm Oleins.' Journal of the Science of Food and Agriculture, 1996, vol. 71, pp. 496-500.
Wai-Lin Stew et al., 'Influence of Diglycerides on the Crystallisation of Palm Oil.' Journal of the Science of Food and Agriculture, 1999, vol. 79, pp. 722-726.
Wai Lin Siew et al: "Diglyceride content and composition as indicators of palm oil quality", Journal of the Science of Food and Agriculture, vol. 69, No. 1, Sep. 1, 1995, pp. 73-79.
Examination Report, European Patent Application No. 11 191 819.9, dated Jul. 3, 2013, 10 pages.

\* cited by examiner

STRUCTURED LIPID COMPOSITIONS

CROSS-REFERENCE TO RELATED APPLICATION

This application is a continuation of U.S. application Ser. No. 11/937,080, filed Nov. 8, 2007, now U.S. Pat. No. 8,486,478 which is incorporated herein by reference in its entirety.

FIELD OF THE INVENTION

The invention generally relates to shortenings and solid fats, and in particular, to shortenings and solid fats incorporating structured lipids having reduced or essentially no trans-unsaturated fatty acids.

BACKGROUND OF THE INVENTION

Dietary fat is one of the most concentrated sources of energy of all the nutrients, typically supplying about 9 kcal/gram, which generally exceeds the caloric content provided by either dietary carbohydrates or protein. Fat contributes to the palatability and flavor of food, since most food flavors are fat-soluble, and to the satiety value, since fatty foods remain in the stomach for longer periods of time than do foods principally containing protein and carbohydrate. Furthermore, fat is a carrier of the fat-soluble vitamins A, D, E, and K and essential fatty acids, which have been shown to be important in growth and in the maintenance of many body functions. Major research efforts have focused on ways to produce food substances that provide similar functional and organoleptic properties as fats at reduced caloric content but which are not readily perceived as being synthetic by consumers.

Natural fats have a broad range of functionalities and are handled in different ways by the human digestive process. A shortening is one type of fat that has a generally high solid fat content at room temperatures and desired melting profiles to provide a certain mouthfeel and organoleptic characteristics. However, such fats may also contain trans-unsaturated fatty acids or saturated fatty acids in forms that are digested and absorbed by the body. Such fatty acids have been linked in recent years to health concerns; however, such fats are generally necessary in the shortening to provide the desired solid fat content and melting profile.

Conventional fat and oil technology has traditionally relied on partial hydrogenation to impart a solid functionality to oils. However, this approach results in oils that contain significant levels of undesired trans-unsaturated fatty acids (TFA's). For example, to form the typical shortening, a liquid vegetable oil is partially hydrogenated to convert the oil into a form suitable for a shortening and produce the desired functionality (hardness and melting profiles suitable for the shortening). The partial hydrogenation, however, can also convert some unsaturated fatty acids in the oil from a cis-orientation to the undesired trans-orientation.

Data in recent years has linked trans-unsaturated fatty acids and some saturated fatty acids to a variety of health concerns. One such health concern, high cholesterol, may be caused, in part, by a diet that includes high levels of such fatty acids. For example, it is now generally accepted that consumption of trans-fatty acids contribute to increased LDL or "bad" cholesterol levels, which may increase the risk of coronary heart disease. Mounting evidence further suggests that, in some individuals, high cholesterol may contribute to increased risk of heart attacks, strokes, and other tissue injuries. There is a desire, therefore, to minimize the amount of trans-fatty acids in foods. Under FDA guidelines, a food or fat can be listed as having zero trans-fatty acids if it contains less than about 0.5 grams of trans-fatty acids per serving. To achieve such levels in a typical baked snack food product, such as a sandwich cookie, the trans-fatty acids in the particular ingredient oils must be kept well below about 3 to about 7 percent. Such levels present challenges in preparing functional shortenings and filler fats having sufficient solid fat content, and desirable organoleptic properties.

In recent years, many efforts have been made to reduce the fat content and the trans-fatty acid content of various foods. However, when the fat level and/or trans-fatty acid level is reduced in conventional foods, the organoleptic and/or functional properties may also be adversely affected. For example, by reducing the level of trans-fatty acids, the hardness and solid fat content is altered so that the fat does not exhibit the desired functionality. In other cases, by reducing the fat content to low levels, the oiliness and/or slipperiness (i.e., mouthfeel) imparted by the fat particles suspended in the food product are effectively lost. In addition, other mouthfeel and textural properties, such as richness and creaminess, may also be adversely affected by the removal or reduction of such fats. Furthermore, flavor properties may be adversely affected because the distribution of flavor molecules between the lipid phase and the aqueous phase is altered. As a result, such reduced-fat food products may not be appealing to the consumer because of their mouthfeel, flavor, and/or organoleptic properties.

U.S. Pat. Nos. 5,879,735 and 5,912,042 describe fat blends comprising diglycerides and triglycerides with long chain saturated and unsaturated fatty acids. The compositions of the '735 patent and the '042 patent, however, have relatively high amounts of fully saturated long chain fatty acids (C12-C24). Fully-saturated, long chain acid diglycerides and triglycerides have relatively high melting points (typically 70-77° C.). Such fat compositions with relatively high melting points are generally more difficult to incorporate into foods, and especially if full melting is required for their incorporation. The disclosures of the '042 and '735 patents state that diglycerides with a relatively high melting point can still be incorporated into foods if combined with another fatty component, such as another diglyceride or triglyceride. These references, however, do not disclose it or how the positioning of the fatty acids on the glycerol backbone affects the properties of the fat blends. These references only indicate that the positioning of the residues in the diglycerides is not very important and provides no disclosure about fatty acid positioning in triglycerides.

As a result, there is a desire to provide a functional fat composition that can be used as a shortening or filler fat, but that has substantially reduced amounts of trans-unsaturated fatty acids, low levels of saturated fatty acids and preferably low levels of bioavailable saturated fatty acids, and a reduced caloric content.

SUMMARY

Lipid compositions are provided exhibiting the functionality of a typical shortening or filler fat, but are achieved with reduced or essentially zero trans-unsaturated fatty acids and low levels of bioavailable saturated fatty acids. Embodiments of the lipid compositions herein preferably form a matrix that is solid, plastic, or spreadable at ambient temperatures with a solid fat content that is sufficient to provide functionality for shortenings and filler fat applications. In addition, the same lipid compositions also have melting profiles that result in minimal or essentially no solid fat content at about body temperature or greater to reduce any waxy mouthfeel or other undesired properties upon consumption. The disclosed lipid compositions also preferably have structures or are configured to hydrolyze into structures during digestion that are poorly absorbed, and therefore, contribute a reduced level of caloric energy. Preferably, the lipid composition comprises either (1) a matrix building ingredient of triglycerides and/or diglycerides diluted with an edible oil or (2) a matrix building ingredient essentially undiluted with oil and having a sufficient amount of saturated fatty acids to form a functional matrix. In each case, the matrix building ingredient comprises a glycerol-based lipid having adjusted content and/or positioning of the acid groups on the glycerol-moiety. By adjusting the content and/or positioning of the acid groups, the melting profiles and ability of the composition to be absorbed during digestion can be affected.

By one approach, the functional lipid compositions herein include a blend of the matrix building ingredient and an edible liquid oil diluent in ratios such that the composition is a functional lipid composition having the properties as generally described above. In this form, the lipid composition has about 5 to about 75 weight percent (preferably about 13 to about 50, and most preferably about 22 to about 50 percent) of the matrix building ingredient and about 25 to about 95 weight percent (preferably about 50 to about 87 percent, and most preferably about 50 to about 78 percent) of the liquid oil diluent. Such compositions will generally have a solid fat content at ambient or room temperatures between about 0.05 to about 60 percent (preferably about 0.1 to about 45 percent, and most preferably about 1 to about 45 percent) and a solid fat content of less than about 10 percent (preferably less than about 2 percent, and most preferably about 0 percent) at about 100° F. or greater. As a result, at ambient temperatures the lipid compositions herein can exhibit a solid, plastic, or spreadable functionality, but at about body temperature when consumed, the lipid compositions generally melt to form liquid phases similar to traditional shortenings. For purposes herein, ambient temperature shall mean about 70° F. to about 80° F. (about 21° C. to about 27° C.).

The edible liquid oil may include any typical vegetable oil or oil blends that are preferably liquid at room temperatures. Examples include, but are not limited to, soybean oil, olive oil, corn oil, palm oil, palm kernel oil, rapeseed oil, cottonseed oil, canola oil, safflower oil, sunflower oil, high oleic oils, and low linolenic oils, and mixtures thereof. Preferably, the lipid compositions herein utilize soybean oil because the desired solid functionality can be obtained in a cost effective manner.

The matrix building ingredient includes a mixture of structured lipids that comprise glycerol esters having the general formula (A):

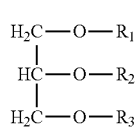

(A)

with $R_1$, $R_2$, and $R_3$ groups. In one form, the matrix building ingredient comprises a mixture of structured glycerol esters in which all three R groups represent an acyl fragment, and the complete structure is a triglyceride or triacylglycerol (TAG). Preferably, at least 50 percent of the TAGs in the matrix building ingredient contain two of the three R groups as long chain, saturated fatty acid residues with between 14 to 24 carbon atoms inclusive (L), with the remaining R group being a short chain acyl fragment with between 2 to 4 carbon atoms inclusive (S) or a medium chain acyl fragment with between 6 to 12 carbon atoms inclusive (M). Most preferably, of the TAGs with two long chain saturated fatty acids, about 60 to about 95 percent have the two L groups located at adjacent glycerol positions (i.e., $R_1$ and $R_2$ or $R_2$ and $R_3$ positions) and about 5 to about 40 percent have the two L groups located at terminal positions (i.e., $R_1$ and $R_3$ positions). Even more preferably, of the TAGs with two long chain saturated fatty acids, about 40 to about 95 percent of the long chain saturated fatty acids are palmitic (C16:0) and/or stearic acid (C18:0) where an excess of the stearic acid is most preferred.

In an alternative form, the matrix building ingredient is a mixture of structured glycerol esters in which only two of the R groups represent a carboxyl or acyl fragment while the third R group represents a hydroxyl function, and the complete structure is a diglyceride or diacylglycerol (DAG). Preferably, at least 20 percent of the DAGs in this alternative mixture contain two of the three R groups that are long chain, saturated fatty acid residues with between 14 to 24 carbon atoms inclusive (L). The remaining DAG structures may comprise combinations of saturated long chain fatty acids (L) and/or unsaturated, long chain fatty acid residues (U). Most preferably, of the DAGs with two long L groups, at least about 20 percent have the two long chain saturated fatty acid residues positioned in both of the terminal groups (i.e., $R_1$ and $R_3$ groups) and/or are positioned in a terminal position (i.e. $R_1$ or $R_3$) and the middle position ($R_2$ group). Even more preferably, the matrix building ingredient includes DAGs with at least 20 percent of structures with L groups located at the terminal glycerol positions in a single molecule. Such matrix building ingredient may also include other diglycerides with saturated or unsaturated long fatty acid chains along with smaller amounts of triglyceride structures as needed to lower the mixtures melting point if desired.

By another approach, the functional lipid compositions herein may also include a matrix building ingredient comprising a diglyceride or diacylglycerol (DAG) with minimal, and preferably, no blended oils. In this form, to obtain the desired functionality, the DAG matrix building ingredient includes sufficient levels of saturated fatty acids to form the desired matrix structures. Preferably, when the lipid compositions is essentially a pure DAG mixture, it has at least about 20 percent, and preferably, about 20 to about 50 percent long chain saturated fatty acids residues (L). The remaining fatty acid residues in the mixture are preferably long chain unsaturated fatty acids (U). It is generally preferred that the fatty acid residues (L) are palmitic (C16:0) and/or stearic acid (C18:0) with an excess of stearic acid more preferred. In this form, the lipid composition generally exhibits a solid fat content of at least about 6 percent, and preferably between about 6 percent and about 45 percent at ambient temperatures, and generally less than about 17 percent, and preferably less than about 10 percent at about 100° F. or greater.

DETAILED DESCRIPTION

Lipid compositions are provided exhibiting the functionality of a typical shortening or filler fat, but are achieved with reduced, and preferably, essentially zero trans-unsaturated fatty acids and low levels of bioavailable saturated fats. The lipid compositions herein are based upon the finding that the functionalities of lipid compositions can be enhanced through the use of structured lipids or structured glycerol esters, which are lipid compositions obtained from the synthesis of triglycerides and diglycerides with control of fatty acid content and location with respect to the glycerol backbone. For purposes herein, a structured lipid or structured glycerol ester shall refer to any glycerol-based lipid with adjusted content and/or positioning of acid groups on the glycerol moiety.

Embodiments of the lipid compositions herein preferably form a matrix of small crystallites that are solid, plastic, or spreadable with a solid fat content that imparts appropriate functionality for application as traditional shortenings or filler fats at ambient/room temperatures. In addition, the same lipid compositions also have melting profiles that result in minimal or essentially no solid fat content at about body temperature or greater to reduce a waxy mouthfeel or other undesired properties upon consumption. The lipid compositions herein also preferably have structures or are configured to hydrolyze into structures during digestion that are poorly absorbed, and therefore, contribute a significantly reduced level of caloric energy. Preferably, the lipid composition comprises either (1) a matrix building ingredient of triglycerides and/or diglycerides diluted with an edible oil or (2) a matrix building ingredient essentially undiluted with oil and having a sufficient amount of saturated fatty acids to form a functional matrix.

As used herein a fat to oil ratio, percentage solid fat, or solid fat content (SFC) is intended to be a characterization of the phase composition of a particular lipid composition. For example, at a certain temperature, a fat is a solid and an oil is a liquid; however, the fat/oil ratio of a given lipid is not constant, but is a function of temperature. That is, for instance, butter can be regarded as mainly solid fat (about 70 percent fat) at 0° C., but becomes plastic at room temperature and completely liquid above about 40° C. As also used herein, functional or a functional lipid composition is also intended to mean a lipid composition as described herein that exhibits a solid fat content such that the composition has properties of a solid shortening or filler fat (i.e., solid, plastic, or spreadable) at or near ambient temperatures. For purposes herein, ambient temperature shall mean about 70 to about 80° F. (about 21° C. to about 27° C.). As also used herein, a long chain saturated fatty acid residue (L) shall mean a carbon chain having between 14 and 24 carbon atoms inclusive; a medium chain saturated fatty acid residue (M) shall mean a carbon chain having between 6 and 12 carbon atoms inclusive; a short chain saturated fatty acid residue (S) shall mean a carbon chain having between 2 and 4 carbon atoms inclusive; and a long chain unsaturated fatty acid residue (U) shall mean a carbon chain having between 14 and 24 carbon atoms inclusive with at least one carbon-carbon double bond.

As discussed further below, the lipid compositions herein include several advantages over traditional shortenings, hard stock triglycerides, and filler fats with high levels of saturated fatty acids and/or trans-unsaturated fatty acids to achieve their desired functionalities. For example, the functional compositions provided herein include negligible and, preferably, essentially no trans-unsaturated fatty acids (TFA), and include triglyceride and/or diglyceride structures that have a reduced caloric content relative to conventional oils (i.e., generally less than about 4-7 kcal/gram of bioavailable energy). In one aspect, the functional compositions herein include less than about 7 percent, preferably less than about 3 percent, and most preferably about 0 percent trans-unsaturated fatty acids. Generally due to the form of the structured glycerol esters, the functional blends herein also reduce the absorption of saturated fats, and depending on the particular formulation, the blends offer the potential to provide a relatively low saturated fat composition with reduced (i.e., less than 0.5 grams TFA's per serving) and, preferably, essentially zero trans-fatty acids that permit labeling foods incorporating the lipid compositions herein as being trans-fatty acid free under current FDA rules.

While not wishing to be limited by theory, it is believed that the byproducts of the natural lipase metabolism of the structured lipids are solids with melt points generally above body temperature (a feature that substantially inhibits their absorption); therefore, the disclosed lipid compositions also provide a reduction in calories from fat along with good gastrointestinal tract tolerance. The preferred structured triglycerides used in the matrix building ingredient undergo preferential hydrolysis of their short and/or medium chain acids during digestion leaving a 1,2-diglyceride residue, which is a solid at body temperature, and therefore poorly absorbed. Alternatively, the matrix building ingredient formed from structured diglycerides also yields glycerol fatty acid esters that reduce absorption and reduce overall calories from fat. For example, it is believed that the preferred structured diglycerides may undergo hydrolysis leaving a 1-monoglyceride residue, which is generally not available for re-synthesis and fat storage.

In addition, the flexibility of the structured lipids permits the ability to construct lipid blends with a variable levels of matrix solids (solid fat content) depending on the desired functionality and application (for example, spreadable, solid, or plastic at room temperature). In this regard, the rates of crystallization and matrix formation may be optimized or varied based on the mixture of fatty acid components in the matrix building ingredient and/or the ratio of edible oil to matrix building ingredient. Moreover, while providing the desired functionality at room temperature, the lipid blends are also essentially, and preferably, melted at body temperatures to minimize, and preferably, eliminate any waxy or other undesired mouthfeel. As such, an individual consuming a food item incorporating the lipid blends experiences a mouthfeel similar to traditional shortenings and filler fats. To that end, the lipid blends herein are sufficiently flexible to be used in formulating processed foods, such as but not limited to, sweet or savory baked goods (i.e., cookies or crackers), snack bars, donuts, pastries, cakes, pies, pizza, processed meats, cheese analogs, ice cream analogs, and the like. The present lipid blends generally provide an oil functionality such as for texture, processing, product stability, and/or a variety of other consumer desired attributes.

By one approach, the disclosed functional lipid compositions include a blend of the matrix building ingredient and an edible liquid oil diluent in ratios such that the lipid composition is a functional lipid composition as generally described above. In one form, the lipid composition has about 5 to about 75 weight percent (preferably about 13 to about 50, and most preferably about 22 to about 50 weight percent) of the matrix building ingredient and about 25 to about 95 weight percent (preferably about 50 to about 87 weight percent, and most preferably about 50 to about 78 weight percent) of the liquid oil diluent. Such compositions generally form a solid matrix with a solid fat content at ambient or room temperatures between about 0.05 to about 60 percent (preferably about 0.1 to about 45 percent, and most preferably about 1 to about 45 percent), and a solid fat content of less than about 10 percent (preferably less than about 2 percent, and most preferably about 0 percent) at about 100° F. or greater. As a result, at ambient temperatures the lipid compositions herein can exhibit a solid, plastic, or spreadable functionality, but at about body temperature when consumed, the lipid compositions melt to form liquids similar to traditional shortenings.

By blending or diluting the matrix building ingredient with the liquid oil, not only can functional lipid compositions be prepared in a cost effective manner (i.e., allowing the amount of a relatively more expensive matrix building ingredient or ingredients to be minimized), but the amount and type of unsaturated and/or polyunsaturated fatty acids provided by the liquid oil in the composition can be selected and tailored to particular applications. That is, for example, the functional lipids herein are sufficiently flexible to employ a wide range of liquid oils into the matrix. In this aspect, the liquid oils have the ability to be sourced from commodity, specialty, or crafted oils depending on the desired functionality, economics, and/or market conditions to suggest but a few examples. As further discussed below, liquid soybean oils are generally preferred for blending with or diluting the matrix building ingredient due to their relatively low cost; however, other liquid oils and/or liquid oil blends may also be employed as desired to construct a functional lipid with the desired amounts of saturated and unsaturated fatty acids, if any.

The edible liquid oil may include any typical vegetable oil or oil blends that are preferably liquid at room temperatures. Examples include, but are not limited to, soybean oil, olive oil, corn oil, palm oil, palm kernel oil, rapeseed oil, cottonseed oil, canola oil, safflower oil, sunflower oil, high oleic oils, low linolenic oils, and mixtures thereof. Preferably, the lipid compositions herein utilize soybean oil because the desired solid functionality can be obtained in a cost effective manner. However, as noted above, other oils or oil blends may be used depending on the application and desired fatty acid composition.

The matrix building ingredient includes a mixture of structured lipid compositions that comprise glycerol esters having the general formula (A):

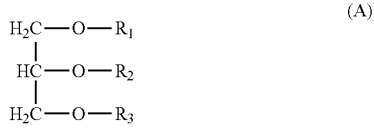

where $R_1$, $R_2$, and $R_3$ groups represent a carboxyl or an acyl fragment (including an aliphatic portion bonded to the glycerol moiety through a carbonyl linkage) or a hydrogen atom forming a hydroxyl group bonded to the glycerol moiety.

In one particular form, the matrix building ingredient comprises a mixture of structured glycerol esters in which all three R groups represent an acyl fragment, and the complete structure is a triglyceride or triacylglycerol (TAG). In such form, at least about 50 percent of the TAGs in the mixture preferably contain two of the three R groups as long chain, saturated fatty acid residues with between 14 to 24 carbon atoms inclusive (L), and the remaining R group is a short chain acyl fragment with between 2 to 4 carbon atoms inclusive (S) or a medium chain acyl fragment with between 6 to 12 carbon atoms inclusive (M).

Preferably, of the TAGs with two long chain saturated fatty acids, about 60 to about 95 percent have the two L groups located at adjacent glycerol positions (i.e., $R_1$ and $R_2$ or $R_2$ and $R_3$ positions) and about 5 to about 40 percent have two L groups located at terminal positions (i.e., $R_1$ and $R_3$ positions). Even more preferably, of the TAGs with two long chain fatty acids, about 40 to about 95 percent are a palmitic acid (C16:0) residue and/or a stearic acid (C18:0) residue where an excess of the stearic acid is most preferred. The remaining or third R group is preferably a short (S) or medium (M) chain fatty acid residue.

Such mixture of triglycerides can be prepared via base catalyzed interesterification to produce a mixture with up to about two-thirds of the triglycerides in the mixture have an unsymmetrical configuration with two adjacent L groups and an S group or an M group at the terminal glycerol positions (i.e., $R_1$ or $R_3$). If desired, a predetermined percentage of long chain saturated fatty acids in the mixture can be obtained through subsequent fractionation, distillation, or other separation methods to remove unwanted or more volatile fatty acids. Alternatively, the triglyceride mixtures suitable for the matrix building ingredient can also be prepared using a lipase catalyzed synthesis to preferentially place specific acids in the desired glycerol positions.

More specifically, a preferred TAG matrix building ingredient comprises a mixture of distearoyl-butyryl-glycerol with at least about 67 weight percent of the mixture including a 1,2-distearoyl-3-butyryl-glycerol. Such mixture may be obtained from a random, base catalyzed interesterification of tributyrin and a fully hydrogenated soybean oil (i.e., about 90 percent stearic acid and about 10 percent palmitic acid). With subsequent fractionation and distillation of more volatile fatty acid triglycerides, a matrix building ingredient having up to about 84 weight percent of distearoyl-butyryl-glycerol may be obtained if desired. For example, a suitable TAG matrix building ingredient for blending with an edible oil has been prepared that includes a mixture of TAGs with about 56 weight percent LLS triglycerides (i.e., 1,2 distearoyl-3-butyryl-glycerol), about 28 weight percent LSL triglycerides (i.e., 1,3 distearoyl-2-butyryl-glycerol), and about 16 weight percent SSL triglycerides (i.e., 1,2 dibutyryl-3-stearoyl-glycerol). These triglyceride products have been shown to deliver about 3.8 kcal/gram of bioavailable energy when fed to rats. (See, e.g., Treadwell, R. M. et al., Journal of Nutrition, V 132, pp. 3356-3362 (2002)). On the other hand, traditional fat delivers about 9 kcal/gram and comparable structures with L and M groups is expected to deliver about 4.2 kcal/gram.

Upon digestion, the above described matrix building ingredient having LLS (or LLM) triglycerides undergo preferential hydrolysis of their terminal S (or M) groups to yield structures that are poorly absorbed. For example, rapid hydrolysis of the short or medium chain via digestive lipase results in 1,2-diglycerides, such as 1,2 distearylglycerol. Such compounds precipitate at body temperatures (melting point of about 77° C.) and are generally not well absorbed. (See, e.g., Dreher et al., Nutrition Today, 33: 164-170 (1998)).

By one approach, the matrix building ingredient including high levels of 1,2-distearoyl-3-butyryl-glycerol, for example, can be blended with the liquid oils, such as soybean oil, to form a functional lipid composition that has sufficient matrix solids at ambient temperatures but essentially no matrix solids at or around body temperature. For example, about 5 to about 75, preferably about 13 to about 50, and most preferably about 22 to about 50 weight percent of the matrix building ingredient can be blended with a liquid oil diluent (i.e., preferably soybean oil) to form a functional lipid composition. Preferably, the matrix building ingredient includes up to about 84 percent TAGs with two L groups, with at least about 56 percent of the TAGs as 1,2-distearoyl-3-butyryl-glycerol. In this form, the lipid composition blend is expected to have a solid fat content of about 0.05 to about 60 percent, preferably 0.1 to about 38 percent, and most preferably about 1 to about 38 percent solid fat at ambient or room temperatures. In addition, the same lipid composition blend will also preferably exhibit a solid fat content of less than about 2, preferably less than about 1 percent, and most preferably exhibit no solid fat content at or above body temperature. In this manner, the lipid-oil blends have the ability to create solid, plastic, or spreadable lipid matrices useful for structuring liquid oils into functional blends at room temperature, but also exhibit an essentially liquid functionality at or above body temperatures to minimize, and preferably, eliminate any waxy or unpleasant mouthfeel upon consumption by a consumer.

In a particularly preferred form, the functional lipid includes about 50 weight percent of the matrix building ingredient blended into soybean oil. The matrix building ingredient includes about 56 percent 1,2-distearoyl-3-butyryl-glycerol. In this preferred form, the lipid-oil blend has a solid fat content of about 22 to about 38 percent at ambient temperature, which is generally higher than the traditional partially hydrogenated vegetable oils that contain high amounts of trans-unsaturated fatty acids to achieve their functionality. At about 100° F., such blend exhibits a solid fat content of less than about 2 percent, which minimizes any waxy mouthfeel. The lipid-oil blends herein, and specifically, the about 50/50 soybean oil and 1,2-distearoyl-3-butyryl-glycerol mixture described above achieves this high solid fat content (at ambient temperatures) with minimal, and preferably, no trans-unsaturated fatty acids.

In another form, the lipid composition includes a blend of a matrix building ingredient diluted in an edible oil, where the matrix building ingredient comprises a mixture of structured glycerol esters in which only two of the R groups represent a carboxyl or acyl fragment while the third R group represents a hydroxyl function. In this form, the matrix building ingredient includes a mixture of diglycerides or diacylglycerols (DAG). Preferably, at least 20 percent of the DAGs in the matrix building mixture contain two of the three R groups that are long chain, saturated fatty acid residues (L) with between 14 to 24 carbon atoms inclusive.

For example, the lipid composition may also include between about 5 and about 50 (preferably about 5 to about 20 percent) percent DAG matrix building ingredient blended into between about 50 and about 95 percent (preferably about 80 to about 95 percent) edible oil diluent. Such lipid compositions sufficiently form the desired matrix and functionality and generally have pleasing organoleptic and mouthfeel characteristics. Higher amounts of the DAG matrix building ingredient may be diluted in oil and still provide the desired functionality, but such compositions may not be organoleptically pleasing due to a waxy mouthfeel.

In this form, the DAG matrix building ingredient preferably includes the two long chain saturated fatty acid residues positioned primarily in both of the terminal glycerol positions (i.e., $R_1$ and $R_3$ groups) with smaller amounts positioned in a terminal position (i.e. $R_1$ or $R_3$) and the middle position ($R_2$ group). The remaining R groups in the glycerol moiety are hydroxyl. In this DAG form of the matrix building mixture, the mixture may also contain other DAGs having combinations of L and/or U acid residues (i.e., LU and/or UU diglycerides). Preferably, these matrix building ingredients are prepared via lipase catalyzed synthesis to preferentially place the fatty acids in the desired positions; however, these diglycerides may also be formed through other suitable procedures. With fatty acid residues primarily in terminal glycerol positions, the diglycerides undergo hydrolysis of one of the terminal L groups to yield a 1-monoglyceride, which is a structure that is generally not available for re-synthesis and fat storage.

More specifically, the DAG matrix building ingredient blended in oil may include a diglyceride mixture having at least about 50 weight percent 1,3-diacylglycerol compounds and at least 30 weight percent 1,2-diacylglycerol compounds. Preferably, the matrix building ingredient includes structures such as 1,3-distearoyl-glycerol and/or 1,2 distearoyl-glycerol. In this form, the lipid composition has a solid fat content of about 4 to about 45 percent at ambient temperatures and about 1 to about 37 percent at about 100° F. or higher (preferably less than about 10 percent at about 100° F. or higher).

In one particular example, about 10 to about 100 weight percent DAG (containing about 20 to about 100 weight percent combined stearic and/or palmitic acids) may be blended into the liquid oil to form a matrix building ingredient. Preferably, about 10 to about 50 percent DAG (containing about 50 to about 100 percent combined stearic and palmitic acids) may be blended into the liquid oil to form a matrix building ingredient. Equally preferred is a matrix building ingredient of about 50 to about 100 percent DAG containing about 20 to about 50 percent combined stearic and oleic acids. In this form, the lipid-oil composition is expected to have a solid fat content at ambient temperatures from about 4 to about 45 percent at ambient or room temperatures. At the same time, this composition also exhibit less than about 36 percent, preferably less than about 14 percent, and most preferably less than about 1 percent solid fat content at or above around body temperature.

In yet another form, the lipid composition comprises a matrix building ingredient of a DAG component essentially undiluted with oil and having a sufficient amount of long chain saturated fatty acid residues to provide the functionalities as described above. In this form, it is preferred to have greater than about 20 percent of the DAGs in the matrix building ingredient having two long chain saturated fatty acids residues (L) with between 14 and 24 carbon atoms inclusive positioned primarily in the terminal glycerol positions. The remaining diglycerides preferably comprise a long chain saturated fatty acids (L) and/or long chain unsaturated fatty acids (U). As with the previous embodiment, these matrix binding ingredients may be prepared via lipase catalyzed synthesis to preferentially place the fatty acids in the desired positions; however, these diglycerides may also be formed through other suitable procedures.

More specifically, a preferred matrix building ingredient that forms the desired functionality when essentially un-diluted with oil includes at least about 60 to about 70 percent 1,3-diacylglcerols compounds and at least about 30 to about 40 percent 1,2-diacylglycerol compounds. Preferably, the matrix building ingredient includes structures such as 1,3-distearoyl-glycerol and/or 1,2-distearoyl glycerol. Even more preferably, the DAG matrix building ingredient includes at least about 20 percent palmitic and/or stearate residues, and more preferably about 20 percent to about 50 percent palmitic and/or stearate residues. In such form, the lipid composition has a solid fat content of at least about 6 percent, and preferably about 6 to about 45 percent at ambient temperatures. Similar to the other embodiments, at about 100° F. or higher, this form of the matrix binding ingredient also minimizes the solid fat content. For example, these DAG ingredients essentially undiluted with oil have a solid fat content less than about 17 percent, preferably less than about 10 percent, and more preferably less than about 2 percent at about body temperature or higher.

When incorporating high amounts of such diacylglycerol compounds into the matrix building ingredient and generally not diluting with an edible oil, a relatively high melting point may be obtained (i.e., about 70 to about 77° C.). A matrix building ingredient with such a high melting point may complicate its incorporation into foods if complete melting is required for such use. In this situation, it is also preferred to include other diacylglyerols or triacylglycerols into the matrix building ingredient to lower its melting point. For example, the DAG matrix building ingredient with a high level of long chain saturated fatty acids may also contain up to about 50 weight percent diacylglycerols with medium chain fatty acids having between 6 and 12 carbon atoms inclusive (M) or short chain fatty acids having between 6 and 12 carbon atoms inclusive (S). Alternatively, the matrix building ingredient may also include moderate amounts (i.e., up to about 50 weight percent) of long chain unsaturated fatty acids (U) having between 14 and 24 carbon atoms inclusive. In either case, the additional glycerol esters are added to the matrix building ingredient as needed to derive the desired melting profile and solid fat profile for the each particular application.

By one approach, a matrix building ingredient including diacylclycerols (DAGs) may be prepared by reacting glycerol and mixtures of oleic acid and stearic acid with a 1,3 specific lipase catalyst to form structures with fatty acids primarily in the terminal glycerol positions. If desired, fractionation and distillation may then be employed to recover the compounds of interest. In this case, after fractionation, the formed matrix building ingredient includes about 25 weight percent UU diglycerides, about 50 weight percent UL diglycerides, and about 25 weight percent LL diglycerides where U is an unsaturated long chain fatty acid with 14-24 carbon atoms inclusive, and L is a saturated long chain fatty acid chain with 14-24 carbon atoms inclusive. Higher amounts of the LL form of the glyceride may be obtained through subsequent fractionation and distillation of more volatile or unwanted fatty acid diglycerides.

The above described matrix building ingredients having triglyceride and/or diglyceride mixtures may also contain other species outside formula (A). Preferred embodiments include mixtures that maximize or concentrate the prescribed product species using special synthetic or random techniques that manipulate the regio-specific placement of chain acid moieties of varying chain length on the glycerol backbone, the reactant ratios, and the reaction conditions. Purification techniques that reduce less desirable triglyceride species may also be employed, for example. It is also desirable to remove low molecular weight triglycerides that provide off flavors.

In preferred glycerol esters, the short moieties (S) are derived from acetic acid, propionic acid, butyric acid, or mixtures thereof. The medium moieties (M) are derived from caproic acid, caprylic acid, capric acid, lauric acid, or mixtures thereof. The long moieties (L) are derived from palmitic acid, stearic acid, arachiadic acid, behenic, or mixtures thereof. And, the long unsaturated moieties (U) are derived from palmitoleic acid, oleyl acid, vaccenic acid, linoleic acid, alpha-linolenic acid, gamma-linolenic acid, gadoleic acid, arachidonic acid, eicosapentaenoic acid, erucic acid, docosahexaenoic acid, or mixtures thereof.

Short or volatile acid residues preferably have no more than 4 carbons. Short residues are derived from carboxylic acids of the formula $S_1COOH$, where $S_1$ is a short chain aliphatic group having 1 to 3 carbons. As denoted herein, where glycerol esters are described as bearing pendant groups derived from acids having 2, 3, or 4 carbons, compositions derived from acids having predominantly 2, 3, or 4 carbons are included. Acylation of a glycerol hydroxyl by acid $S_1COOH$ results in the attachment of short chain S or $S_1$ to the glycerol backbone by means of an ester linkage (—O—(CO)—). Where there is more than one short group attached to a glyceride, the groups may be the same or different. As used herein, the term "acid residue" refers to an acyl group comprising a short chain portion, a medium chain portion, or a long chain portion, and a carbonyl group.

Short chain acyl groups S may be straight or branched and may be derived from any synthetic or natural organic acid including, but not limited to, acetic (ethanoic), propionic (propanoic), butyric (butanoic), and the like acids. As used herein, chemical names include isomeric variations; for example, "butyric acid" includes normal butyric acid (butanoic acid) and iso butyric acid (2 methylpropanoic acid), and so forth. Preferred acids are acetic acid, butyric acid, mixtures of acetic and butyric acids, mixtures of acetic and propionic acids, and mixtures of acetic, propionic, and butyric acids.

Medium chain acyl groups M are derived from any synthetic or natural organic medium chain fatty acid of the formula $M_1COOH$, including, but not limited to caproic (hexanoic), caprylic (octanoic), pelargonic (nonanoic), capric (decanoic), lauric (dodecanoic) and the like acids. Preferred medium chain fatty acids contain predominantly (i.e., at least about 75 percent), and preferably at least about 90 percent, caprylic acid, capric acid, or mixtures of these acids.

Unsaturated long chain U groups are also present in the mixtures. They may be monounsaturated or polyunsaturated. Unsaturated lipid oils comprising fatty acids and lipids incorporating fatty acid moieties are of particular interest and suitability for use in the present invention as a source of U groups. The fatty acid chains in these lipid oils can be straight, branched, or ring structures. Preferably, the fatty acid chains are straight hydrocarbon chains ("straight" embraces cis and/or trans main chain configurations). By one approach, the fatty acids or lipid containing fatty acid moieties are amphipathic (i.e., have both hydrophilic and hydrophobic groups). Examples of suitable unsaturated lipids include many readily available vegetable, animal, and marine oils containing long chain fatty acids or moieties thereof. The invention is especially useful in the treatment of unsaturated triglyceride oils, polyunsaturated fatty acid oils, and other long chain unsaturated fatty acid oils. Again, lipid oils having straight alkyl chains in the fatty acid moieties are preferred.

The unsaturated long chain acyl groups U are derived from unsaturated acids of the formula $U_1COOH$, where $U_1$ is a C15 to C19 unsaturated group. These include, but are not limited to, palmitoleic (9 hexadecenoic), oleic (cis 9 octadecenoic), elaidic (trans 9 octadecenoic), vaccenic (trans 11 octadecenoic), linoleic (cis, c is 9,12 octadecedienoic), linolenic (9,12,15 octadecatrinoic and 6,9,12 octadecatrienoic), eleostearic (9,11,13 octadecatrienoic), arachidonic (5,8,11,14 eicosatetraenoic), and the like acids. Various U groups (and saturated long chain groups (L), if applicable) can be derived from mixtures of fatty acids obtained from natural oils such as soybean, safflower, sunflower, sesame, peanut, corn, olive, rice bran, mustard seed, cottonseed, poppyseed, rapeseed, marine, meadowfoam, and the like oils; fats such as babassu nut oil, palm oil, tallow, lard, shea butter, and the like; or plant waxes such as jojoba.

Starting materials for triglyceride preparations may be obtained commercially or isolated from natural sources. Alternatively, component triglycerides may be isolated from natural or processed fats or oils, or fractions thereof. If needed or desirable, mixtures can be purified using steam deodorization, filtration, fractional distillation, and similar purification methods.

The following examples are included to illustrate the invention and not to limit it. Unless otherwise stated, all parts and percentages are by weight. All patents, references, and publications referenced herein are hereby incorporated by reference in their entirety.

EXAMPLES

Example 1

A structured glycerol ester composition was prepared via a base catalyzed interesterification to form a triglyceride mixture primarily having glyceride esters with two long chain saturated fatty acids and one short chain fatty acids. To produce this structured lipid, a mixture of fatty acid constituents, as defined in Table 1 below, was randomly interesterified in the presence of a catalytic amount of sodium methoxide (about 0.3%) with vigorous stirring at 125° C. for 20 minutes. The resulting crude mixture was fractionated through a wiped-film evaporator at about 0.1 Torr to remove the more volatile triacylglycerols that had only one long chain fatty acid. The residue from the evaporator was further distilled to produce a cream colored solid that contained about 84 weight percent triacylglycerols with two long chain saturated fatty acids and one short chain fatty acid. The composition of the resultant mixture (as measured by capillary high temperature GC of intact triacylglycerols) is summarized in Table 2 below and comprises one example of a matrix building ingredient for the lipid compositions herein.

TABLE 1

| Reactants | |
|---|---|
| Reactant | Amount (grams) |
| Tributyrin (Aldrich Chemical) | 906 |
| Fully hydrogenated soybean oil (AC Humko) (90% Stearic acid, 10% palmitic acid) | 440 |

TABLE 2

| Composition of Structured Glycerol Esters in mixture | |
|---|---|
| Structure | Amount (%) |
| LLS | 56 |
| LSL | 28 |
| LSS | 11 |
| SLS | 5 |

Using the methodology of Finley (Finley et al., "Growth Method for Estimating the Caloric Availability of Fats and Oils," J. Agric. Food Chem., Vol. 42, 489-494 (1994)) feeding studies in rats have shown a product with the composition of Table 2 to deliver about 3.8 kcal/gram of bioavailable energy. An unstructured composition with a comparable complement of long and medium chain fatty acids would be expected to deliver about 4.2 kcal/gram of bioavailable energy. While not wishing to be limited by theory, it is believed that the reduction in bioavailable energy is a result of poor absorption of stearic and palmitic acids from the dominate SGE forms (LLS and/or LLM).

Example 2

The structured lipid composition prepared in Example 1 was blended with various amounts of soybean oil (AC Humko) as defined in Table 3. The blends were then melted in a microwave oven to produce clear liquids. The samples were analyzed by pulsed NMR according to AOCS Official Method Cd 16b-93 to measure the equilibrium solid or solid fat content at different temperatures. The results are provided in Table 3. For comparison, two control oils were also tested having various levels of trans-unsaturated fatty acids: (1) soy spray 2 oil (SS2) (ADM) having about 42 to about 45 percent trans-unsaturated fatty acids and about 20 percent saturated fatty acids; and (2) LTB-1 oil (Kraft Foods) having about 78 percent soybean oil and about 22 percent partially hydrogenated cottonseed oil having less than about 8 percent trans-unsaturated fatty acids.

TABLE 3

| | Solids Fat Content (SFC) | | | | | |
|---|---|---|---|---|---|---|
| | Amount SGE, % | | | | SS2 | LTB1 |
| Temp, ° C. | #1 13% | #2 22% | #3 30% | #4 50% | (High TFA Control) | (Low TFA Control) |
| 0 | 12.3 | 23.9 | 32.7 | 52.5 | 65 | 24.5 |
| 10 | 6.2 | 18.5 | 28.1 | 49.1 | 47 | 14 |
| 21.1 | 0.1 | 3.2 | 14.6 | 38.7 | 20 | 11 |
| 26.7 | 0 | 1 | 1.6 | 22.7 | 14 | 10 |
| 33.3 | 0 | 0.7 | 1.4 | 2.6 | 4 | 6 |
| 37.8 | 0 | 0.4 | 0.5 | 2.4 | 0 | 3 |
| 40 | 0 | 0 | 0.4 | 1.7 | 0 | 0 |
| 42.5 | 0 | 0 | 0 | 1.3 | 0 | 0 |
| 45 | 0 | 0 | 0 | 0.9 | 0 | 0 |
| 47.5 | 0 | 0 | 0 | 0 | 0 | 0 |

Depending on the desired solids functionality, the test oil sample numbers 3 and 4 had a generally equal or greater solids fat content at ambient temperatures (about 21° to about 27° C.) (about 70° F. to about 80° F.) than the high TFA control, but still had comparable levels of solids fat content at about body temperature of about 38° C. (about 100° F.).

Example 3

The four test samples from Example 3 were warmed in a microwave oven at full power for sufficient time to produce clear liquids. Each liquid was allowed to cool without agitation at ambient temperatures (about 25° C.) and over the course of about 1 hour the ability of each sample to form a solid matrix was observed. The observations are provided in Table 4 below.

TABLE 4

| Observations | | | |
|---|---|---|---|
| Sample 1 | Amount SGE, % | Amount Oil, % | Observation |
| 1 | 13 | 87 | some solid suspended in liquid oil |
| 2 | 22 | 78 | gel forms slowly |
| 3 | 30 | 70 | gel forms slowly |
| 4 | 50 | 50 | rapidly forming opaque gel |

When the samples were fully equilibrated to ambient temperature (~25° C.), samples 2-4 could be inverted with little or no liquid draining indicating their ability to function as a solid fat matrix at ambient temperatures.

Example 4 (Comparative Example)

A partially hydrogenated soybean oil shortening (Soybean Spray Oil) (ADM) was analyzed by pulsed NMR as in Example 2. The results are provided in Table 5 below.

TABLE 5

| Comparative Solid Fat Content of a Partially Hydrogenated Shortening | |
|---|---|
| Temperature, ° C. | Solid Fat Content, % |
| 21.1 | 20 |
| 26.7 | 14 |
| 33.3 | 4 |
| 37.8 | 0 |

Comparing the results of this example to sample 4 in Example 2, the lipid-oil blend in sample 4 had substantially more matrix solids at ambient temperatures (21-27° C.) or (70-80° F.) than the comparative partially hydrogenated shortening of this example. At ambient temperatures, the composition of sample 4 in Example 2 had 22 to 38 percent solid fat content, while the comparative shortening only had 14 to 20 percent solid fat. Moreover, sample 4 also had a similar solid fat content at or above body temperatures (about 38° C. or about 100° F.).

Example 5

A structured glycerol ester composition was prepared using a 1,3 specific lipase catalyst to form a matrix building ingredient including a mixture of 1,3-diacylgylcerides. Glycerol (Aldrich Chemical) and mixtures of oleic acid (Nu-Chek Prep, Elysian, Minn.) and stearic acid (Nu-Chek Prep) as defined in Table 6 below were exposed to a vacuum at about 150 Torr at about 55° C. and a 1,3 specific lipase catalyst (Lipozyme Rmim, Noro Novodisk). The contact was maintained for about 1.5 to 2.5 hours to permit substantial conversion to 1,3 diacylglycerol compounds. The DAG composition was separated from the catalyst by filtration, dried, and subjected to short path (molecular) distillation to remove unreacted fatty acids to obtain the matrix building ingredient as described in Table 6 below.

TABLE 6

Reactants

| Description | Amount, grams |
|---|---|
| Glycerol | 14.0 |
| Oleic Acid | 68.8 |
| Stearic Acid | 17.2 |
| Enzyme | 20 |

The composition of Table 6 was distilled to various stearate levels and analyzed for solid fat content as described above in Example 2. The results are summarized below in Table 7.

TABLE 7

Solid Fat Content

| Temp, ° C. | Stearate Content in Matrix Building Ingredient. | | | | |
|---|---|---|---|---|---|
| | 20% | 25% | 30% | 40% | 50% |
| 0 | 46.9 | 53.2 | 63.3 | 70.5 | 78.3 |
| 10 | 39.0 | 45.4 | 55.6 | 62.6 | 70.8 |
| 21.1 | 11.8 | 17.5 | 25.7 | 36.4 | 49.6 |
| 26.7 | 6.1 | 9.2 | 17.6 | 29.3 | 42.4 |
| 33.3 | 2.8 | 4.9 | 9.4 | 18.9 | 30.8 |
| 37.8 | 1.8 | 2.9 | 5.4 | 10.4 | 17.2 |

Example 6

Functional lipid compositions having 20 and 25 percent stearate (as described in Example 5 above) and 80 and 75 percent unsaturates, respectively, were analyzed for solid fat content and compared to various traditional shortenings: super Hymo (AC Humko), a cream cookie filler (ADM), butter chip (Golden Brands). The fat compositions were analyzed for solid fat content as in Example 2 and the results are provided in Table 8.

TABLE 8

Solid Fat Content

| Temp, ° C. | Super Hymo (Comparative) | Cream Cookie Filler (Comparative) | Butter chips (Comparative) | 80/20 DAG (Inventive) | 75/25 DAG (Inventive) |
|---|---|---|---|---|---|
| 0 | 52.7 | 72.4 | 89.1 | 47.4 | 53.6 |
| 10 | 47.9 | 66.8 | 87.3 | 39.8 | 45.3 |
| 21.1 | 28.2 | 44.1 | 73.5 | 12.9 | 18.4 |
| 26.7 | 20.1 | 27.8 | 56.2 | 6.7 | 10.1 |
| 33.3 | 13.1 | 11.9 | 30.9 | 2.5 | 4.5 |
| 37.8 | 8.8 | 4.8 | 14.4 | 1.5 | 2.8 |

Example 7

A DAG composition with about 10 percent palmitic acid and about 87 percent stearic acid obtained from a fully saturated vegetable oil was examined for solid fat content alone and dissolved in soybean oil. The solid fat content of the DAG composition alone (100 percent) and the DAG composition blended with soybean oil is provided in Table 9.

TABLE 9

Solid fat content (%) of a lipid composition having various amounts of DAG matrix building ingredient blended in oil.

| T (° C.) | Amount of DAG Matrix Building Ingredient in Oil | | | | | |
|---|---|---|---|---|---|---|
| | 100%* | 40% | 30% | 20% | 10% | 5% |
| 0 | 98.9 | 44.3 | 33.5 | 22.6 | 11.8 | 5.9 |
| 10.0 | 98.6 | 44.4 | 34.0 | 22.5 | 11.3 | 5.7 |
| 15.6 | 98.5 | 44.5 | 33.8 | 22.3 | 11.8 | 5.4 |
| 21.1 | 98.4 | 44.4 | 33.1 | 21.8 | 10.9 | 4.6 |
| 26.7 | 98.1 | 43.6 | 31.6 | 19.9 | 9.5 | 4.0 |
| 33.3 | 98.0 | 40.4 | 28.9 | 17.8 | 7.3 | 2.7 |
| 37.8 | 97.7 | 35.8 | 24.8 | 14.5 | 5.1 | 1.3 |
| 40.0 | 97.7 | 35.8 | 24.8 | 14.5 | 5.1 | 1.3 |
| 45.0 | 96.9 | 29.7 | 19.6 | 9.6 | 2.6 | 0.4 |
| 50.0 | 94.3 | 20.0 | 12.0 | 5.8 | 0.7 | 0 |
| 55.0 | 78.4 | 11.2 | 5.7 | 2.0 | 0 | — |
| 60.0 | 32.2 | 4.7 | 1.7 | 0 | — | — |
| 65.0 | 16.4 | — | — | — | — | — |
| 70.0 | 0 | — | — | — | — | — |

*essentially no oil diluent.

The data in Table 9 above show that modest levels of a fully saturated DAG can provide a source of functional matrix in a liquid vegetable oil. While all lipid compositions summarized above in Table 9 generally formed functional matrices, with solid fat contents greater than about 10 percent at about 100° F. or higher, these lipid compositions may not be organoleptically pleasing due to a waxy mouthfeel, but could be suitable for some applications.

It will be understood that various changes in the details, materials, and arrangements of parts and components which have been herein described and illustrated in order to explain the nature of the methods and compositions may be made by those skilled in the art within the principle and scope as expressed in the appended claims.

What is claimed is:

1. A matrix building ingredient comprising a mixture of glycerol esters having the formula:

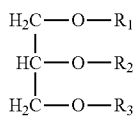

wherein the R groups each represent an acyl fragment, wherein at least about 50 weight percent of the glycerol esters in the mixture have two of the $R_1$, $R_2$, and $R_3$ groups as long chain saturated fatty acid residues with between 14 to 24 carbon atoms inclusive and the remaining R group being a short chain acyl fragment with between 2 to 4 carbon atoms inclusive or a medium chain acyl fragment with between 6 to 12 carbon atoms inclusive, and of the glycerol esters having two of the $R_1$, $R_2$, and $R_3$ groups as long chain saturated fatty acid residues, there are more glycerol esters having long chain saturated fatty acid residues in adjacent glycerol positions than in terminal glycerol positions,
  wherein the matrix building ingredient comprises up to about 84 percent triglycerides with two long chain saturated fatty acid residues with at least about 56 percent of the triglycerides comprising 1,2-distearoyl-3-butyryl-glycerol.

2. The matrix building ingredient of claim 1, wherein the lipid composition is essentially free of trans-unsaturated fatty acids.

3. The matrix building ingredient of claim 1, wherein the glycerol esters having two of the $R_1$, $R_2$, and $R_3$ groups as long chain saturated fatty acid residues include about 60 to about 95 percent having long chain saturated fatty acid residues in adjacent glycerol positions.

4. The matrix building ingredient of claim 3, wherein the glycerol esters having two of the $R_1$, $R_2$, and $R_3$ groups as long chain saturated fatty acid residues include about 5 to about 40 percent having long chain saturated fatty acid residues in terminal glycerol positions.

5. The matrix building ingredient of claim 1, wherein the matrix building ingredient includes a mixture of palmitic acid residues and stearate residues and wherein the matrix building ingredient includes more stearate residues than palmitic acid residues.

6. The matrix building ingredient of claim 5, wherein the glycerol esters having two of the $R_1$, $R_2$, and $R_3$ groups as long chain saturated fatty acid residues include about 40 to about 95 percent stearate.

7. The matrix building ingredient of claim 1, wherein the matrix building ingredient further comprises a mixture of diglycerides and at least about 20 weight percent of the diglycerides in the mixture have two of the $R_1$, $R_2$, and $R_3$ groups as long chain saturated fatty acid residues.

8. The matrix building ingredient of claim 7, wherein the matrix building ingredient includes more diglycerides having long chain saturated fatty acid residues in terminal glycerol positions than adjacent glycerol positions.

9. A matrix building ingredient comprising a mixture of diglycerides with at least about 20 percent of the diglycerides having two long chain saturated fatty acid residues with between 14 and 24 carbon atoms inclusive positioned in terminal glycerol positions,
  wherein the matrix building ingredient comprises includes about 20 to about 50 percent palmitic acid and/or stearate residues and has a solid fat content of at least about 6 percent at ambient temperatures.

10. The matrix building ingredient of claim 9, wherein the remaining diglycerides comprise long chain saturated fatty acids and/or long chain unsaturated fatty acids.

11. The matrix building ingredient of claim 9, the matrix building ingredient comprising about 60 to about 70 percent 1,3-diacylglycerol compounds and about 30 to about 40 percent 1,2-diacylglycerol compounds.

12. The matrix building ingredient of claim 9, wherein the diglyceride mixture comprises at least about 50 percent of 1,3-di-stearoyl-glycerol and at least about 30 percent of 1,2-di-stearoyl-glycerol.

13. The matrix building ingredient of claim 12, wherein the matrix building ingredient is essentially free of trans-unsaturated fatty acids.

14. A matrix building ingredient comprising a mixture of glycerol esters having the formula:

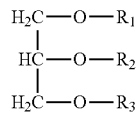

wherein the R groups each represent an acyl fragment, wherein at least about 50 weight percent of the glycerol esters in the mixture have two of the $R_1$, $R_2$, and $R_3$ groups as long chain saturated fatty acid residues with between 14 to 24 carbon atoms inclusive and the remaining R group being a short chain acyl fragment with between 2 to 4 carbon atoms inclusive or a medium chain acyl fragment with between 6 to 12 carbon atoms inclusive, and of the glycerol esters having two of the $R_1$, $R_2$, and $R_3$ groups as long chain saturated fatty acid residues, there are more glycerol esters having long chain saturated fatty acid residues in adjacent glycerol positions than in terminal glycerol positions,
  wherein the matrix building ingredient includes a mixture of palmitic acid residues and stearate residues and wherein the matrix building ingredient includes more stearate residues than palmitic acid residues.

15. The matrix building ingredient of claim 14, wherein the lipid composition is essentially free of trans-unsaturated fatty acids.

16. The matrix building ingredient of claim 14, wherein the glycerol esters having two of the $R_1$, $R_2$, and $R_3$ groups as long chain saturated fatty acid residues include about 60 to about 95 percent having long chain saturated fatty acid residues in adjacent glycerol positions.

17. A matrix building ingredient comprising a mixture of glycerol esters having the formula:

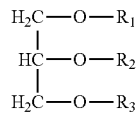

wherein the R groups each represent an acyl fragment, wherein at least about 50 weight percent of the glycerol esters in the mixture have two of the $R_1$, $R_2$, and $R_3$ groups as long chain saturated fatty acid residues with between 14 to 24 carbon atoms inclusive and the remaining R group being a short chain acyl fragment with between 2 to 4 carbon atoms inclusive or a medium chain acyl fragment with between 6 to 12 carbon atoms inclusive, and of the glycerol esters having two of the $R_1$, $R_2$, $R_3$ groups as long chain saturated fatty acid residues, there are more glycerol esters having long chain saturated fatty acid residues in adjacent glycerol positions than in terminal glycerol positions, wherein the matrix building ingredient further comprises a mixture of diglycerides and at least about 20 weight percent of the diglycerides in the mixture have two of the $R_1$, $R_2$, and $R_3$ groups as long chain saturated fatty acid residues.

18. The matrix building ingredient of claim 17, wherein the lipid composition is essentially free of trans-unsaturated fatty acids.

19. The matrix building ingredient of claim 17, wherein the glycerol esters having two of the $R_1$, $R_2$, and $R_3$ groups as long chain saturated fatty acid residues include about 60 to about 95 percent having long chain saturated fatty acid residues in adjacent glycerol positions.

* * * * *

UNITED STATES PATENT AND TRADEMARK OFFICE
CERTIFICATE OF CORRECTION

PATENT NO. : 8,911,813 B2  
APPLICATION NO. : 13/913825  
DATED : December 16, 2014  
INVENTOR(S) : Lawrence Paul Klemann and Robert C. Dinwoodie It is certified that error appears in the above-identified patent and that said Letters Patent is hereby corrected as shown below:

In the claims

Column 18, line 64, in claim 17, delete "R2, R3" and insert --R2, and R3--.

Signed and Sealed this
Twenty-sixth Day of July, 2016

Michelle K. Lee
*Director of the United States Patent and Trademark Office*